United States Patent [19]

Odom

[11] Patent Number: 5,840,320
[45] Date of Patent: Nov. 24, 1998

[54] METHOD OF APPLYING MAGNESIUM-RICH CALCIUM MONTMORILLONITE TO SKIN FOR OIL AND ORGANIC COMPOUND SORPTION

[75] Inventor: Ira Edgar Odom, Bartlett, Ill.

[73] Assignee: AMCOL International Corporation, Arlingon Heights, Ill.

[21] Appl. No.: 548,101

[22] Filed: Oct. 25, 1995

[51] Int. Cl.[6] .............................. A61K 7/48; A61K 7/50
[52] U.S. Cl. ................ 424/401; 424/78.03; 424/78.1; 424/78.07; 424/78.05; 424/722; 424/744; 514/887; 514/844; 514/830; 514/828; 514/949; 514/770
[58] Field of Search ........................... 424/401, 78.03, 424/78.1, 78.07, 78.05, 722, 744; 514/887, 844, 830, 828, 949, 770

[56] References Cited

U.S. PATENT DOCUMENTS

| | | | |
|---|---|---|---|
| 1,736,375 | 11/1929 | Sherick | 252/1 |
| 1,943,519 | 1/1934 | Denning | 37/5 |
| 1,943,584 | 1/1934 | Cross | 252/6 |
| 2,231,328 | 2/1941 | Simons | 255/1 |
| 3,697,643 | 10/1972 | Sheperd et al. | 424/63 |
| 3,853,781 | 12/1974 | Haschke et al. | 252/132 |
| 4,279,547 | 7/1981 | Clem | 405/258 |
| 4,462,470 | 7/1984 | Alexander et al. | 175/72 |
| 5,061,397 | 10/1991 | Goodman | 252/174.25 |

Primary Examiner—Raj Bawa
Attorney, Agent, or Firm—Marshall, O'Toole, Gerstein, Murray & Borun

[57] ABSTRACT

A method of increasing the bulk density and improving the water-dispersibility, oil sorption capacity, and body dirt and oil removability by compacting and/or shearing a magnesium rich calcium montmorillonite clay. In an optional embodiment of the present invention, silica gel, sodium silicate, acrylic polymers and copolymers, carboxy methyl cellulose, or other materials capable of providing lubricity to the surface of the clay crystals is added to the clay, prior to shearing, to enhance the compaction and/or shearing process and further increase the bulk density of the clay. The clay is sheared in an extruder, pug mill or California-type pellet mill when the clay includes about 20% to about 45%, preferably about 25% to about 40% by weight water, based on the dry weight of the clay.

13 Claims, 5 Drawing Sheets

METHOD OF APPLYING MAGNESIUM-RICH CALCIUM MONTMORILLONITE TO SKIN FOR OIL AND ORGANIC COMPOUND SORPTION

FIELD OF THE INVENTION

The present invention is directed to a method of applying a high magnesium content calcium bentonite paste to human body skin to clean the skin, remove dead skin cells, and to sorb organic compounds, such as secreted insect chemicals, for reducing or eliminating itching, e.g., from mosquitos. The present invention also is directed to a method of increasing bulk density of relatively low density (less than about 45 pounds/ft$^3$) montmorillonite clays while providing the clay with a coating of silica gel, thereby increasing the water-dispersibility, water-absorption and water-adsorption properties of the clay, and reducing dust during manufacturing and handling, thereby increasing the potential economic use of the clay as a desiccant. More particularly, the present invention is directed to a method for increasing the bulk density, water-absorption, water-adsorption and water-dispersibility properties of a low-bulk density montmorillonite or bentonite, such as Carmargo Earth—a magnesium (Mg+$^2$ or MgO) rich calcium bentonite that occurs naturally in northwestern Oklahoma.

BACKGROUND OF THE INVENTION

Common Montmorillonite clays, such as sodium bentonite and calcium bentonite, that have dense textures, relatively high bulk densities, e.g., 55–70 lb/ft$^3$, and typical magnesium contents, e.g., less than about 4% MgO, usually less than about 3.5% MgO by weight, have been extruded or pug milled for the purpose of aligning clay layers (crystals) and to form pellets from the clay particles, e.g., for decreasing fluid loss in oil wells against loss of drilling muds, to increase viscosity of aqueous solutions, and the like. Examples of patents that disclose extrusion of montmorillonite clays include the following: Simons U.S. Pat. No. 2,231,328; and Alexander and Odom U.S. Pat. No. 4,462,470.

In accordance with the present invention, shearing calcium montmorillonite clay that is high in magnesium content, as defined by having at least 4% by weight magnesium (measured as MgO), preferably at least about 4.5% by weight magnesium, provides the clay with new and unexpected skin cleansing properties, as evidenced in the ability to sorb (absorb and/or adsorb) body oils, to remove dead skin cells and to separate dirt particles from skin and remove the dirt particles, oils and cells by rinsing away with water.

In addition, the preferred magnesium-rich calcium montmorillonite that is sheared in accordance with the present invention, has increased surface area, increased bulk density and increased capacity for water-absorption making the clay an excellent desiccant.

SUMMARY OF THE INVENTION

In brief, the present invention is directed to a method of increasing the bulk density and improving the water-dispersibility, oil sorption capacity, and body dirt and oil removability by compacting and/or shearing a magnesium rich calcium montmorillonite clay. In an optional embodiment of the present invention, silica gel, sodium silicate, acrylic polymers and copolymers, carboxy methyl cellulose, or other materials capable of providing lubricity to the surface of the clay crystals is added to the clay, prior to shearing, to enhance the compaction and/or shearing process and further increase the bulk density of the clay. The clay is sheared in an extruder, pug mill or California-type pellet mill when the clay includes about 20% to about 45%, preferably about 25% to about 40% by weight water, based on the dry weight of the clay.

Accordingly, one aspect of the present invention is to provide a magnesium-rich montmorillonite clay-based skin cleaner capable of new and unexpected capacity for removal of oil and dirt, and insect secretions from animal skin, particularly from human skin, and the adsorption of insect secretions.

Another aspect of the present invention is to provide a method of increasing the bulk density of a magnesium-rich calcium montmorillonite clay for desiccant purposes.

These and other aspects and advantages of the present invention will become more apparent from the following detailed description of the preferred embodiments, taken in conjunction with the drawings.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE PREFERRED EMBODIMENTS

The preferred calcium montmorillonite clay that has a high magnesium content, useful for the compositions and methods of the present invention, is called "CARMARGO EARTH". Carmargo Earth is a natural calcium montmorillonite clay material that occurs in northwestern Oklahoma. Like other bentonites, Carmargo Earth was formed from the alteration of volcanic glass. However, the volcanic glass from which Carmargo Earth formed contained a higher amount of magnesium than almost all other forms of bentonite.

The predominant mineral contained in Carmargo Earth is a magnesium-rich form of the clay mineral called calcium montmorillonite. The only other occurrences of a high magnesium montmorillonite are in eastern Arizona and near San Diego, California. These bentonites, however, are grayish in color, whereas Carmargo Earth is light pink. The pink color is due to a high content of $Fe_2O_3$.

Figure 1:
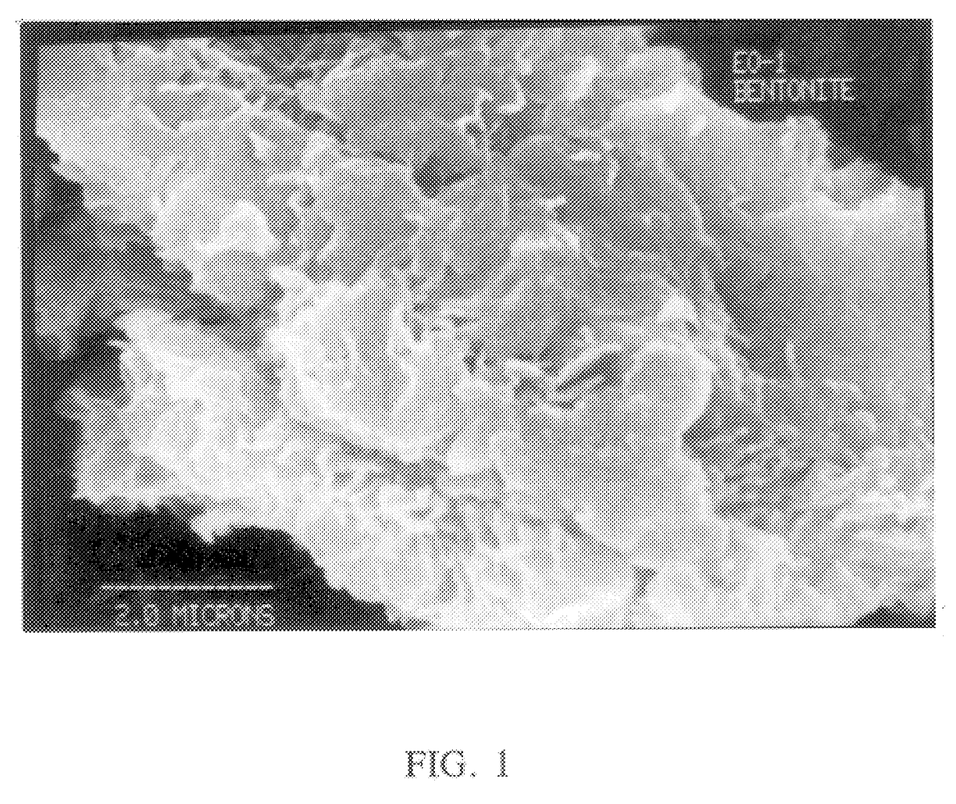
FIG. 1 is an electron micrograph of Carmargo Earth showing the small size of the individual crystals.

Carmargo Earth has unique adsorption characteristics, chemical composition, particle size, and color. The high content of magnesium (MgO) in Carmargo Earth imparts unusual adsorptive properties to the surface of the montmorillonite crystals. The crystals have a high layer charge due to the high amount of substitution of $Mg^{+2}$ for $Al^{+3}$ in the crystal structure. In addition, the montmorillonite crystals in Carmargo Earth are very small, less than 1 micron in size (FIG. 1). One gram of Carmargo Earth has a total surface area in excess of 500 square meters. The unique pinkish color is due to a high $Fe^{+3}$ content.

Figure 3:
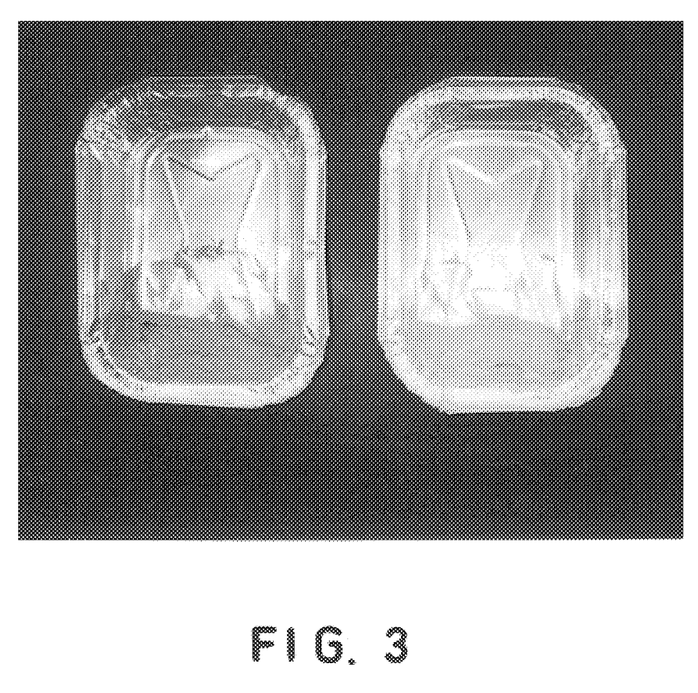
FIG. 3 is a photograph of Carmargo Earth (right) compared to a darker, grey colored Arizona magnesium-rich montmorillonite (left)
Figure 4:
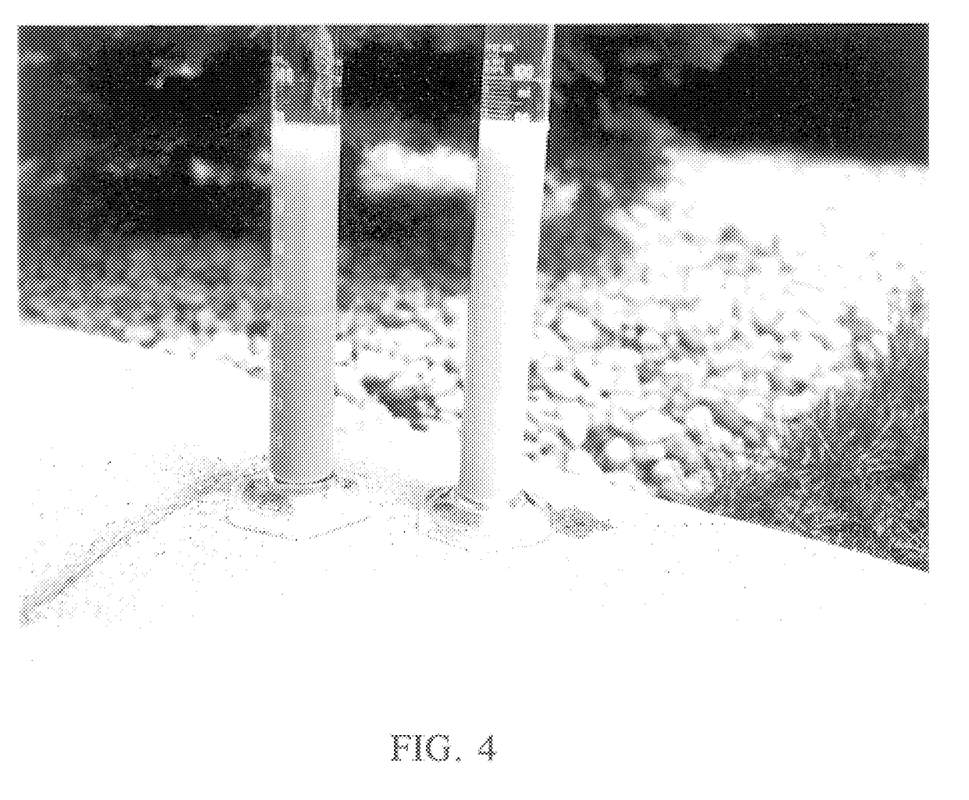
FIG. 4 is a photograph showing the water dispersibility of Carmargo Earth (right) compared to Arizona montmorillonite (left) after five minutes of setting time.
Figure 5:
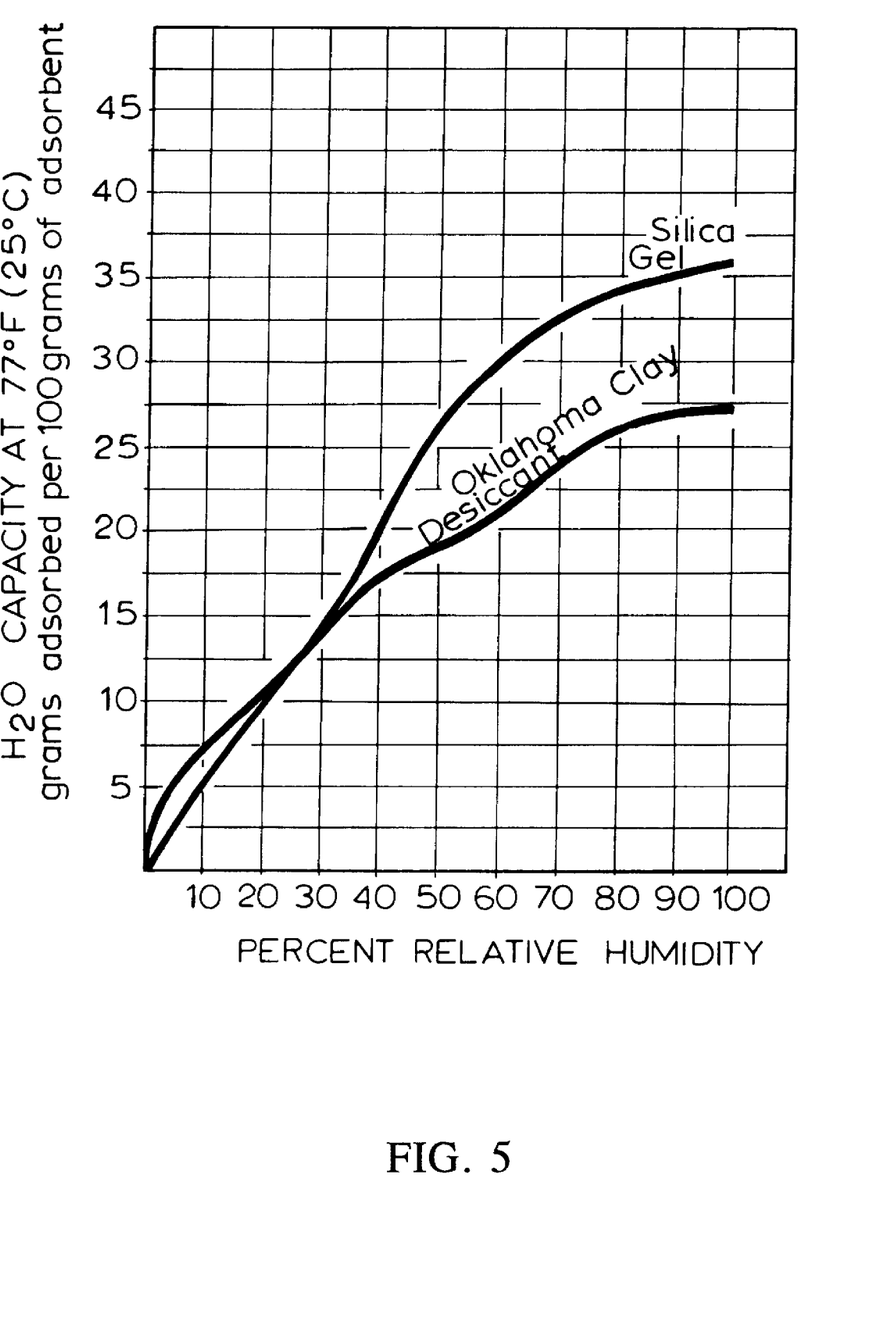
FIG. 5 is a graph showing the moisture adsorption characteristics of Carmargo Earth (Oklahoma clay desiccant) compared to the moisture adsorption of silica gel, showing that Carmargo Earth has greater moisture adsorption than silica gel at less than about 30% relative humidity.

There is no other high charge, pinkish-colored, small crystal size bentonite known at the present time. It is unique in both color and in chemical composition. The color is light pink due to its small amount of ferric iron. The montmorillonite composing Carmargo Earth has a high content of magnesium. The $Mg^{+2}$ or $MgO$ content is twice as much as occurs in Wyoming Na bentonites or in calcium bentonites from Mississippi or Texas. Table 1 shows the chemical composition of Carmargo Earth compared to Arizona, California, Wyoming, Mississippi and Texas bentonites. It can be seen that only the Arizona and California bentonites have a similar MgO content, but both of these bentonites are gray in color. Both the Arizona and California bentonites contain considerable black manganese which causes their color in slurry, powder, and paste forms to be dark gray to nearly black (FIGS. 3 and 4).

Figure 2:
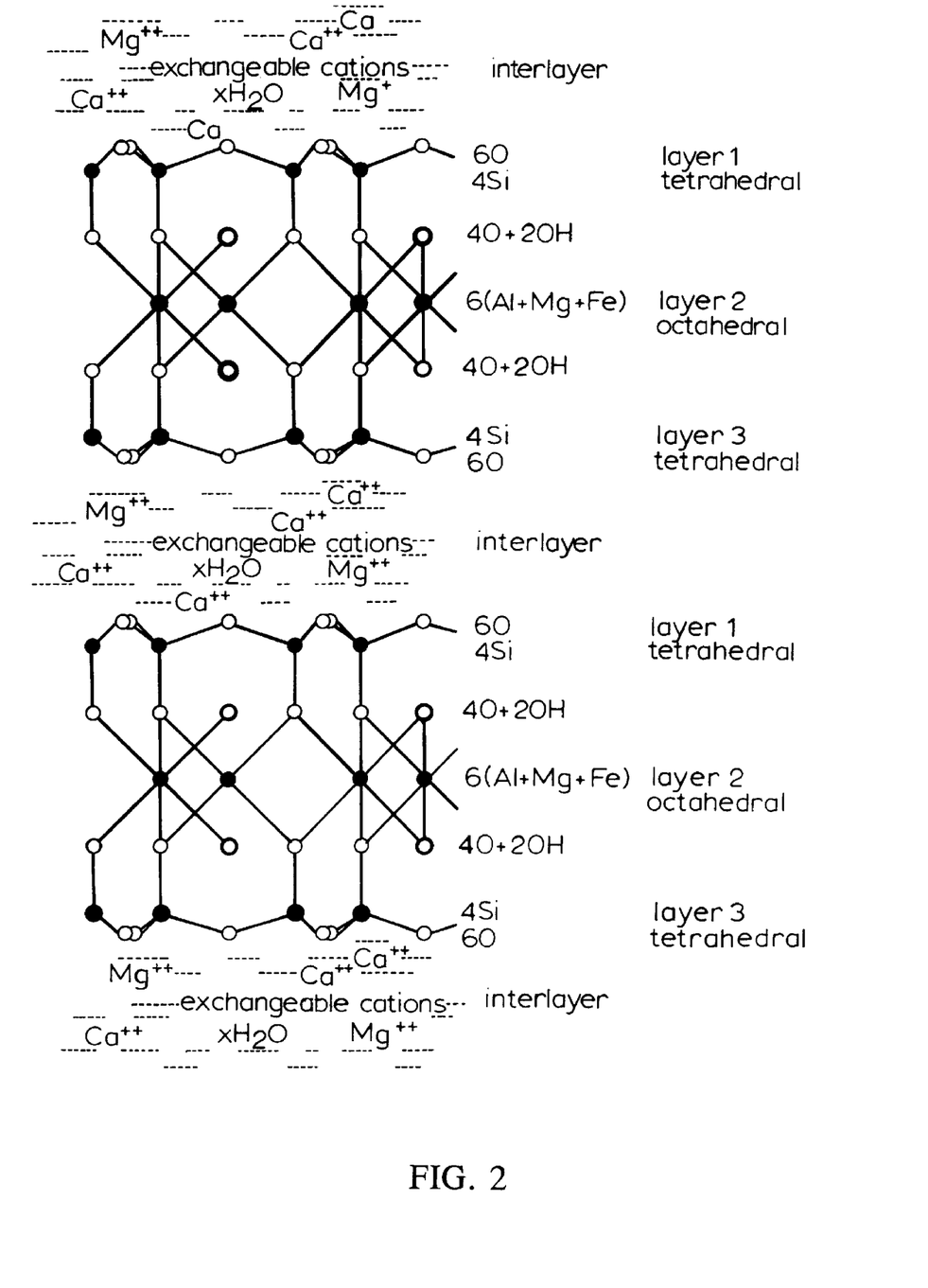
FIG. 2 is a schematic representation of the structure and chemical composition of magnesium-rich montmorillonite.

The structure and chemical composition of Mg-rich montmorillonite is shown in FIG. 2. Most of the MgO in Carmargo Earth substitutes for $Al^{+3}$ in the octahedral or middle sheet of the three sheet layer structure (FIG. 2). The substantial substitution of $Mg^{+2}$ for $Al^{+3}$, compared to most other bentonites (FIG. 2) causes a high net negative electrical charge per formula unit or unit cell of the Carmargo Earth montmorillonite crystals (Table 1).

This high charge is reflected to the basal surfaces of the crystals, and is only partially balanced by positively charged, exchangeable $Ca^{+2}$ and $Mg^{+2}$ ions that occur on the crystal surfaces (FIG. 2). In Carmargo Earth, unlike most other bentonites, at least one fourth of the $Al^{+3}$ cations in the octahedral sheet are replaced by $Mg^{+2}$ cations. This chemical characteristic distinguishes Carmargo Earth montmorillonite from the montmorillonite composing most other bentonites.

Due to the high layer charge, Carmargo Earth has a very high cation exchange capacity (112 to 135 meq/100 g) as compared to most other bentonites (Table 2). It is the magnitude of the unbalanced unit cell negative charge that is responsible for the high degree of body oil adsorption, skin wrinkle reduction, the efficient removal of positively charged dirt particles, the removal of dead cells covering skin pores and the deep cleaning of skin wrinkles and pores, including sorption of toxic chemicals left in the skin by insects, such as mosquitos, and the like. The clay is mixed with water to form a paste composition containing about 5% to about 80% liquid carrier, preferably about 15% to about 80% by weight liquid carrier—preferably water or a mixture of water and an organic solvent, e.g., $C_1$—$C_3$ alcohol—more preferably about 20% to about 60% by weight liquid carrier, e.g., water, most preferably about 30% to about 50% by weight liquid carrier, e.g., water. It is possible to add small amounts of certain kinds of liquid organic-based detergents so long as the organic compound is not adsorbed on the basal surfaces of the clay particles to the extent that it destroys the adsorptive properties of the clay crystals for body oils, and the like.

Carmargo Earth should be sterilized, e.g., by heating to about 250° F. to 500° F. prior to its use in body and hand paste products. Because of the sterilization and the high cleaning and organic compound sorption efficiency of Carmargo Earth, skin surfaces contacted with Carmargo Earth are ultra hygienic and clean, as can be verified easily by microscopic examination. Paste forms of Carmargo Earth are prepared in stainless steel tanks with boiling hot distilled water so that no germs can be transmitting to the skin's surface.

In addition to body oils and other natural organic skin secretions, Carmargo Earth adsorbs many other organic substances such as motor oil, gasoline, various kinds of chemicals used in beauty shops, poison ivy sap, and poison from insect bites when applied onto the organic substance, preferably immediately after exposure, allowed to dry and absorb the organic substance for a few minutes, e.g., preferably at least about 5 minutes. Carmargo Earth will also remove oils and several kinds of stains from cloth and

TABLE 1

BENTONITE CHEMICAL COMPOSITIONS

|  | $SiO_2$ | $Al_2O_3$ | $TiO_2$ | $Fe_2O_3$ | MnO | MgO | CaO | $Na_2O$ | $K_2O$ | LOI | Layer Charge |
|---|---|---|---|---|---|---|---|---|---|---|---|
| Carmargo Earth, Oklahoma | 61.70 | 17.30 | 0.57 | 3.95 | 0.03 | 6.79 | 3.18 | 0.06 | 0.08 | 6.51 | 0.99 |
| Chambers, Arizona | 61.77 | 19.85 | 0.24 | 1.95 | — | 5.56 | 1.89 | 0.07 | 0.09 | 7.72 | 0.97 |
| Otay, California | 62.23 | 21.03 | — | 2.23 | — | 5.70 | 0.08 | 0.65 | — | 7.38 | 0.86 |
| Colony, Wyoming | 62.0 | 23.5 | — | 3.72 | — | 1.95 | 0.31 | 2.87 | 0.03 | 6.45 | 0.75 |
|  | 62.9 | 19.3 | 0.16 | 3.85 | 0.01 | 2.80 | 1.80 | 1.54 | 0.56 | 5.10 | Unknown |
| Aberdeen, Mississippi | 59.73 | 21.82 | — | 5.54 | 0.01 | 2.10 | 2.48 | 0.80 | 0.22 | 6.59 | 0.66 |
| Gonzales, Texas | 69.6 | 16.3 | 0.29 | 1.21 | 0.01 | 3.56 | 1.73 | 0.33 | 0.15 | 7.50 | Unknown |

TABLE 2

CATION EXCHANGE CAPACITY (meq/100 g)

| Oklahoma | 132* |
| Arizona | 120* |
| Wyoming | 85* |
| California | ? |
| Mississippi | 80* |
| Texas | 88* |

*Measured by methylene blue adsorption test.

leather when applied onto the stain and allowed to absorb after drying for a few minutes, e.g., preferably at least about 5 minutes. In the same manner, Carmargo Earth aids in the healing of fever sores, and reduces the itch of insect bits due to its strong adsorptive properties for poisons related to these skin problems.

Carmargo Earth has a pleasing, pinkish flesh-like color when prepared in granular, powder or paste forms. FIG. 3 shows the color of Carmargo Earth (right) compared to Arizona bentonite when both are prepared in paste form. Carmargo Earth is pinkish and flesh-like in appearance, whereas the Arizona bentonite is dark gray. The pinkish color of Carmargo Earth is due to ferric iron. Although the Arizona bentonite contains some iron, it is mostly the ferrous ($Fe^{+2}$) ions which impart a black or greenish color. From a color standpoint, Carmargo Earth is strongly favored over the Arizona bentonite for facial and body cleaning applications because of its pleasing pink color when wet and pinkish white color when dry. The moisture content of paste formed of Carmargo Earth usually should range from about 25% to about 80% by weight, depending on the paste stiffness desired.

Carmargo Earth can be used as a desiccant, preferably after compaction to increase its bulk density to approximately the same value as the bulk density of the commonly used Arizona bentonite (about 56–68 lbs/cu/ft). Also, the compaction process makes the Oklahoma bentonite much more dispersible in water than the Arizona bentonite. FIG. 4 shows agueous dispersions of Oklahoma and Arizona bentonites after both were subjected to compaction. The Oklahoma bentonite disperses and remains in suspension, whereas the Arizona bentonites tends to rapidly settle from suspension. The Oklahoma bentonite is superior to the Arizona and California bentonites for body cleansing because of its higher degree of dispersibility.

The high degree of dispersibility makes the Oklahoma bentonite far more effective as a facial and body cleaner due to the greater amount of surface area that is available for absorption and adsorption.

WHAT CARMARGO EARTH DOES

1. Removes organic and inorganic liquids, oils and impurities (dirt) from skin's surface and pores.

2. Removes dead surface cells and exposes newer, younger skin.

3. Provides thorough, deep cleaning of skin, pores, and wrinkles.

4. Removes skin's shine for many hours.

5. Refines skin's texture.

6. Strongly contracts pores and wrinkles if permitted to dry on skin.

7. Silkens the skin's touch as it eases and contracts lines.

8. Makes the skin supple and soft.

9. Excellent for skin preparation prior to or in conjunction with the application of moisturizer(s).

10. Recommended for all skin types, especially acne-prone skin. Does not need to include scrubbing grains which could irritate blemishes. However, silica sand, pumice, volcanic ash and other abrasive materials may be combined with Carmargo Earth to loosen grease, ink stains, and other organic materials from the skin.

11. Adsorbs poisons and other organic liquids associated with certain skin problems such as poison ivy, insect bites, fever sores, and the like.

RECOMMENDED APPLICATION AND USE OF CARMARGO EARTH AS A FACE MASK

1. Rub a thin, continuous layer of Carmargo Earth paste onto the skin. Continue to rub paste over skin to evaporate water until paste begins to thicken. Make sure all parts of skin are covered, except for eyes and lips.

2. Leave Carmargo Earth paste in contact with facial skin until completely dry. Paste will dry to a whitish color. A hair dryer can be used on low heat to speed drying. Paste should be completely dry for most effective contraction of wrinkles and pores. Skin will begin to tighten as paste dries. For best results, leave dried paste in contact with skin for at least five minutes.

3. Remove dried Carmargo Earth by washing face with warm water followed by rubbing face with a warm wet facial cloth.

4. Carmargo Earth is recommended for deep application of moisturizers, make ups and other skin care products.

5. Skin will have a cool feel after Carmargo Earth is removed. This is the result of deep cleaning of pores and the skin's surface, and the removal of dead surface cells. The cool feel is due to a higher evaporation rate from the skin which evaporation rate is increased due to the deep cleansing achieved.

6. It is recommended that Carmargo Earth not be used more than once in each 24-hour period. Carmargo Earth is especially effective for treating acne-prone skin.

RECOMMENDED USE OF CARMARGO EARTH AS A HAND AND BODY CLEANER

1. Rub a thick continuous layer, e.g., 0.5–3 mils, of Carmargo Earth paste over area to be cleaned. Continue to rub paste until it begins to become stiff. Make sure all parts of the skin or hands are covered, without application to the eyes or lips.

2. Let Carmargo Earth paste remain in contact with skin for one to two minutes or until it begins to dry. Skin will begin to tighten as paste begins to dry.

3. Remove Carmargo Earth by liberally washing with warm water followed by rubbing the treated skin with a warm, wet facial cloth.

4. Carmargo Earth is recommended for deep cleaning of skin prior to the application of moisturizers, makeup and other skin care products.

5. The skin will have a cool feel after Carmargo Earth is removed. This feeling is normal, and is the result of the deep cleaning of pores and the skin's surface, and the removal of dead surface cells.

6. It is recommended that Carmargo Earth not be used more than once in each 24-hour period. Carmargo Earth is especially recommended for acne-prone skin.

RECOMMENDED APPLICATION AND USE OF CARMARGO EARTH TO REDUCE ITCH FROM INSECT BITES

Carmargo Earth is effective in removing poisons from insect bites. The effectiveness of Carmargo Earth in relieving the itch caused by insect bites, mosquito, black flies, sand flies, chiggers, nosee'm, bees, and the like, is related to the length of time after the bit that the paste is applied. The sooner the earth is applied, the better will be the results.

1. Rub a thick layer, e.g., 0.05–0.5 mm of Carmargo Earth paste over and around the bit area continue to rub paste over and into bit area until paste thickens. Be sure that a thick layer remains on the bite area.

2. Let paste dry completely and remain in contact with the bite area preferably for at least about 5 minutes, more preferably at least about 30 minutes making sure bite area remains completely covered. The longer the dried paste remains in contact with the skin, the more effectively the poisons are removed.

3. Paste may be removed from skin by washing bite area with water or rubbing with a wet wash cloth. Repeat steps 1 and 2 if itching should reoccur.

METHOD OF COMPACTION-DESICCANT USE

Compaction of Carmargo Earth is accomplished in the preferred embodiment by the use of an extruder, preferably equipped with a pug chamber, a de-airing chamber, a sealing die and a point auger. The front face or chamber of the extruder is equipped with a die containing holes one-eighth inch to one inch in diameter. The holes are drilled with a taper that contracts down stream so that compression is increased when the clay is forced through the holes, e.g., by an auger. A California type pellet mill also may be used for compaction.

The pressure required to produce a bulk density of about 54–58 pounds per cubic foot is accomplished by equipping the extruder with a variable speed motor. The variable speed motor permits a nearly constant pressure to be maintained even though the clay feed rate may vary.

In the compaction process, colloidal silica gel, sodium silicate, or some other friction reducing compound, e.g., a cross-linked metal salt of polyacrylic acid or carboxymethylcellulose, is metered into the clay at the back end of the pug unit of an extruder or before introducing the clay into a California type pellet mill. An extruder pug unit is favored because the silica gel is more completely mixed in with the moist crude clay. The crude clay preferably has a moisture content between about 20% and about 45% by weight, based on the dry clay, preferably about 25% to about 35%, for maximum bulk density increase during compaction and for maximum coating of the clay mineral crystals by the silica gel during mixing.

During the compaction process, the bulk density can be varied by changing the diameter of the holes in the extrusion extruder die plate. However, the smaller the die holes, the lower will be the production rate. A larger hole diameter is possible by holding the die plate pressure constant through the variable speed motor. The compacted clay described in Table 3 was extruded on a commercial scale through one half inch diameter die holes. The sample described in Table 3 that was compacted in the laboratory was extruded through a die having three-eighths inch diameter holes.

TABLE 3

Compaction of Oklahoma Calcium Bentonite (Minus 6 Mesh plus 30 Mesh Granules)

| | Bulk Density (without Compaction) | Bulk Density After Compaction without Silica Gel | Bulk Density with 1% Silica Gel |
|---|---|---|---|
| Laboratory Compaction | 42 lbs/cu/ft | 52 lbs/cu/ft | 56 lbs/cu/ft |
| Commercial Compaction | 42 lbs/cu/ft | 51 lbs/cu/ft | 57 lbs/cu/ft |

TABLE 4

Dust Yield From Compacted and Uncompacted Oklahoma Calcium Bentonite (−6 + 8 mesh granules)

| | *Percent Dust |
|---|---|
| Crude Clay | 8.17 |
| Compacted Clay (1% Silica Gel) | 0.12 |

*Dust production and granule hardness was determined by placing 50 grams of −6 + 8 mesh granules of crude and compacted (1% silica gel) on a 10 mesh screen. The screen was placed on a shaking table and shaken for five minutes at a rate of 400 R.P.M.

An additional discovery of this invention is that compacted Oklahoma Calcium bentonite, when dried to less than 10 percent moisture, is much more dispersible in water than is compacted Calcium bentonite from Arizona, Texas or Mississippi. FIG. 4 shows the high degree of dispersibility of Oklahoma compacted calcium bentonite compared to Arizona compacted calcium bentonite. The properties in certain uses of Oklahoma compacted calcium bentonite are greatly improved as a result of the high degree of crystal dispersion that results in more available surface area. The dispersibility resulting from the compaction process is a key factor in the high degree of body oil adsorption and dirt particle removal that is displayed by Oklahoma calcium bentonite.

Due to its chemical composition, the Oklahoma calcium bentonite has potential to be used as a clay desiccant, but in its natural form, after drying to zero percent moisture, its bulk density is much too low. Standard size desiccant packages that require a 32–36 gram desiccant unit weight are too small to accept a light weight clay desiccant. The compaction process increases the bulk density to nearly the same value as Arizona calcium bentonite that is now used extensively as a clay desiccant. An experiment done on the compaction of Arizona bentonite showed very little increase in bulk density. Before compaction, the bulk density of Chambers, Arizona calcium bentonite was 58 lbs/cu/ft. Compaction increased the bulk density only one pound to 59 lbs/cu/ft. Oklahoma calcium bentonite shows a dramatic increase in bulk density with compaction because it has an open texture. It has many tiny holes filled with air. The compaction pressure and shear force removes the pores and brings the clay particles into a far more compact arrangement. Like the Chambers, Arizona calcium bentonite, Wyoming sodium bentonite and Mississippi and Texas calcium bentonites do not show a significant increase in bulk density with compaction.

This invention also is directed to a compaction process that increases the bulk density of a calcium bentonite from 42 lbs/cu ft. to 54–58 lbs/cu ft. or to approximately the same bulk density as other calcium bentonites used for clay desiccants. Because of the compaction process disclosed herein, a 32–36 gram desiccant unit can be achieved, and the reduced volume permits the clay desiccant manufactured from compacted clay to fit the space available in standard size desiccant cloth and paper packages. In the uncompacted form, the volume of the clay is too large to be packaged in standard desiccant bags used to package higher bulk density desiccant grade clays. The bulk density of Carmargo Earth is increased by the compaction process because in its natural form, the texture of the clay includes considerable void pore space (filled with air).

In accordance with the present invention, the shear forces resulting from the compaction process produces a bentonite product having a markedly high degree of dispersibility when the subject clay is slurried in water (e.g., 50–95% water); or prepared in a paste form (e.g., 20–80% water). The higher dispersibility greatly improved the absorptive and adsorptive properties of the Mg-rich calcium montmorillonite. The improved dispersibility makes the Oklahoma calcium bentonite a superior product for use as a hand and body cleaner and as a facial mask product. These uses are augmented by the natural pinkish color of the calcium montmorillonite when prepared in powder or paste forms from Carmargo Earth.

The addition of about 0.05% to about 10%, preferably about 0.5% to about 1% by weight colloidal silica gel or sodium silicate to the crude clay prior to compaction essentially prevents dust production during granulation of the clay and subsequently during handling of the granular materials. Also, the lubricity imparted by silica gel or other lubricant compound produces a higher bulk density (Table 3). Although other colloidal gels, i.e., silica gel, sodium silicate, organic polymers, and the like can be used to impart lubricity, silica gel and/or sodium silicate are preferred because of their desiccant properties. The clay desiccant with silica gel, after drying to the required zero moisture level, shows no decrease in its ability to remove moisture from air and other gases.

Bulk Density of Arizona Bentonite Before
Compaction 58 lb/cu ft. after compaction 59 lb/cu
ft.

The bulk density of the Arizona bentonite is 58 to 59 lb/cu/ft after compaction both with and without silica gel. Thus, the bulk density of Arizona bentonite before compaction and after compaction is essentially the same, which indicates that the natural form of the Arizona bentonite does not contain pores filled with air. The texture of the Arizona bentonite is very dense.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the structure may be varied substantially without departing from the spirit of the invention, and the exclusive use of all modifications which come within the scope of the appended claims is reserved.

What is claimed is:

1. A method of cleaning skin comprising contacting the skin with a composition comprising a mixture of a calcium montmorillonite clay and a liquid, said calcium montmorillonite clay having at least about 4% by weight magnesium, measured as MgO, said composition comprising liquid in an amount of about 5% to about 80% by weight, and about 20% to about 95% of said calcium montmorillonite clay; and washing the composition from the skin.

2. The method of claim 1, wherein the liquid comprises water.

3. The method of claim 2, wherein the liquid consists essentially of water.

4. The method of claim 1, wherein the composition comprises about 20% to about 60% by weight water and about 40% to about 80% by weight of said calcium montmorillonite clay.

5. A method of reducing skin wrinkles comprising contacting the wrinkles with a mixture of a calcium montmorillonite clay and a liquid, said calcium montmorillonite having at least about 4% by weight magnesium, measured as MgO, said composition comprising liquid in an amount of about 5% to about 80% by weight, and about 20% to about 95% of said calcium montmorillonite clay; allowing the composition to dry; and washing the composition from the skin.

6. The method of claim 2, wherein the liquid comprises water.

7. The method of claim 6, wherein the liquid consists essentially of water.

8. The method of claim 5, wherein the composition comprises about 20% to about 80% by weight water and about 20% to about 80% by weight of said calcium montmorillonite clay.

9. A method of reducing itching associated with an insect bite comprising covering the insect bite with a composition comprising a mixture of a calcium montmorillonite clay and a liquid, said calcium montmorillonite clay having at least about 4% by weight magnesium, measured as MgO, said composition comprising liquid in an amount of about 5% to about 80% by weight, and about 20% to about 95% of said calcium montmorillonite clay; and washing the composition from the skin.

10. The method of claim 9, wherein the insect bite is a mosquito or chigger bite.

11. The method of claim 9, wherein the liquid comprises water.

12. The method of claim 11, wherein the liquid consists essentially of water.

13. The method of claim 9, wherein the composition comprises about 20% to about 80% by weight water and about 20% to about 80% by weight of said calcium montmorillonite clay.

* * * * *

UNITED STATES PATENT AND TRADEMARK OFFICE
CERTIFICATE OF CORRECTION

PATENT NO. : 5,840,320
DATED : November 24, 1998
INVENTOR(S) : Odom

It is certified that error appears in the above-identified patent and that said Letters Patent is hereby corrected as shown below:

Title page,
Item [56], References Cited, after 1,736,375 11/1929 please delete "Sherick" and insert -- Sherrick --.

Column 3,
Line 3, after "substitution of Mg..." delete "$^{+hu\ 2}$" and insert -- $Mg^{+2}$ --.

Column 5,
Line 4, after "the itch of insect..." delete "bits" and insert -- bites --.

Column 6,
Line 64, after "of time after the..." delete "bit" and insert -- bite --.
Line 66, after "over and around the..." delete "bit" and insert -- bite --.

Signed and Sealed this

Twenty-fifth Day of December, 2001

Attest:

*Attesting Officer*

JAMES E. ROGAN
*Director of the United States Patent and Trademark Office*